United States Patent [19]

Bullard et al.

[11] 3,963,442

[45] June 15, 1976

[54] COLORIMETRIC INDICATOR COMPOSITIONS AND METHOD OF MANUFACTURE

[76] Inventors: Wade A. Bullard, Sturgis, Mich.; Donald B. Stahlman, Indianapolis, Ind.

[22] Filed: Dec. 4, 1974

[21] Appl. No.: 529,343

[52] U.S. Cl. .......................... 23/253 TP; 23/230 R; 23/230 B; 116/114 AM; 252/408
[51] Int. Cl.² .......................................... G01N 31/22
[58] Field of Search ............... 23/253 TP; 252/408; 116/114 AM

[56] References Cited
UNITED STATES PATENTS

| | | | |
|---|---|---|---|
| 3,002,385 | 10/1961 | Wahl | 23/253 TP |
| 3,006,735 | 10/1961 | Jordan | 23/253 TP |
| 3,642,450 | 2/1972 | Eriksson | 23/253 TP |
| 3,723,064 | 3/1973 | Liotta | 23/253 TP |
| 3,784,358 | 1/1974 | Drake | 23/253 TP |
| 3,798,004 | 3/1974 | Zerdchid | 23/253 TP |
| 3,809,616 | 5/1974 | Schmitt | 23/253 TP |
| 3,810,739 | 5/1974 | Nussbaum | 23/253 TP |

*Primary Examiner*—Morris O. Wolk
*Assistant Examiner*—Sidney Marantz
*Attorney, Agent, or Firm*—Miller, Morriss, Pappas & McLeod

[57] ABSTRACT

Colorimetric indicator compositions and their method of manufacture. A first reagent composition is included in the indicator compositions so that when a second reagent composition is applied to an exposed surface of the indicator compositions a reaction occurs to produce a color change. The indicator compositions include as one component a thermoplastic resin which is soluble in a liquid carrier for the second reagent composition at ambient temperatures. Particularly preferred indicator compositions incorporate a particulate coloring or contrast agent in the resin which, when the liquid carrier containing the second reagent composition is applied on an exposed surface of the indicator compositions containing the first reagent composition, dissolves the resin at the surface to provide a contrasting color background of dispersed particles in the liquid carrier. The indicator compositions are preferably prepared by coating particles of the thermoplastic resin with the first reagent composition and then thermoplastically bonding the particles together by conventional molding techniques. This method produces islands of the first reagent composition between bodies of the thermoplastic resin. Test strips utilizing the indicator compositions and their method of use.

29 Claims, 6 Drawing Figures

COLORIMETRIC INDICATOR COMPOSITIONS AND METHOD OF MANUFACTURE

DESCRIPTION OF INVENTION

The present invention relates to colorimetric indicator compositions, their method of manufacture and use, including test strips, which incorporate a first reagent composition which is to be reacted with a second reagent composition applied to an exposed surface of the indicator compositions in a liquid carrier to produce a color change. In particular, thermoplastic resins are used as the base for the compositions in an amount such that the compositions would disperse if immersed for an extended period of time in the liquid carrier for the second reagent composition.

PRIOR ART

The prior art has produced a variety of colorimetric indicator devices. Such devices currently use paper or other liquid absorptive or adsorptive porous media as a support matrix for a first reagent composition. When a second reagent composition in a liquid carrier is applied to the support matrix, the carrier floods the matrix so that the first and second reagent compositions react to produce a color change which indicates the presence of the second reagent in the liquid carrier. Such devices are described for instance in U.S. Pat. No. 2,854,317 and find wide medical use.

The prior art devices function well when there is a clear color contrast produced by the reacted first and second reagents; however, in many instances the support matrix masks the color change to a certain degree making it difficult to evaluate the results of the test. Usually the test results are evaluated qualitatively since there is not great variance of color as a function of the concentration of the second reagent composition. Where the amount of the second reagent composition is marginal in terms of producing a color change, detection can be difficult. It is believed that this result is produced in part because of non-uniform or selective migration of the first reagent composition in the support matrix away from an exposed surface of the support matrix during manufacture. Migration of the reacted first and second reagents compositions away from an exposed surface also reduces color change visibility.

A significant limitation of the prior art support matrix devices is that they are not reusable. Once the second reagent composition in the liquid carrier permeates the support matrix and reacts with the first reagent composition, the available first reagent composition is used up for practical purposes. Once used, the prior art indicators are discarded.

The methods for the preparation of the prior art support matrix devices also require considerable care in the selection and processing of the matrix and in the introduction of the first reagent composition into the matrix and thus are expensive. If the support matrix is non-uniform in its absorptive properties treatment from batch to batch, its testing function is rendered unreliable. In one such device which is being marketed the support matrix is glued to a plastic holder or handle and the glue permeating the matrix contributes to possible non-uniform distribution of the first reagent composition.

Another limitation of the prior art indicator devices is that they usually cannot be preserved for future reference with the reacted first and second reagent compositions for long periods. Once the support matrix has dried, the color which was provided by the reacted first and second reagents fades or disappears altogether and can only partially be revived by rewetting the matrix.

OBJECTS

The objects of the present invention are to provide a colorimetric indicator which overcomes these prior art limitations. In particular, it is an object of the present invention to provide colorimetric indicator compositions which can be easily and economically manufactured and yet are completely reliable from batch to batch in yielding reproducible test results. It is further an object of the present invention to provide semi-quantitative results where there is a progressive color change depending upon the concentration of ingredients of the second reagent composition. Further still it is an object of the present invention to provide compositions which are reusable for test purposes and which can be preserved with the reacted reagent colors. These and other objects will be increasingly apparent by reference to the following description and to the drawing.

IN THE DRAWING

DETAILED DESCRIPTION OF THE INVENTION

Figure 1:
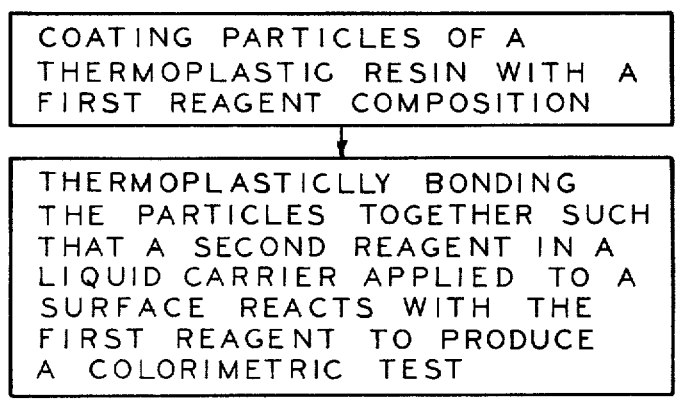
FIG. 1 is a schematic diagram of the steps of the preferred method of the present invention.

The present invention particularly relates to a colorimetric indicator composition which comprises a first reagent composition which is reactive with a second reagent composition applied in a liquid carrier to produce an identifiable color, a solid body of thermoplastic resin which is soluble in the liqid carrier for the second reagent composition at ambient temperatures and mixed with the first reagent composition in an amount sufficient for at least a qualitative colorimetric detection of the second reagent composition in the liquid carrier which is applied to an exposed surface of the resin and dissolves the resin at the surface without permeating the body of the resin. It also relates to the preferred method of manufacturing the colorimetric indicator compositions which comprises a first reagent composition which is reactive with a second reagent composition applied in a liquid carrier to produce an identifiable color; coating particles of a thermoplastic resin which is soluble in the liquid carrier for the second reagent composition at ambient temperatures with a first reagent composition; and thermoplastically bonding the particles together into a solid body so that the first reagent composition is dispersed throughout the resin, the amount of first reagent being sufficient for at least a qualitative colorimetric detection of a solution containing the second reagent which is applied to an exposed surface in a liquid carrier which dissolves the resin at the surface without permeating the body of the resin.

The present invention further relates to a preferred test device wherein a first reagent composition in the device which is reactive with a second reagent composition applied to the device in a liquid carier produces an identifiable color which comprises a support strip including a handle and a body portion; at least one part provided on the body portion and being comprised of a solid body of a thermoplastic resin which is soluble in the liquid carrier for the second reagent composition at ambient temperatures in admixture with the first reagent composition in an amount sufficient for at least a qualitative colorimetric detection of the second reagent composition which is applied to an exposed surface of the resin in a liquid carrier which dissolves the resin at the surface without permeating the body of the resin.

The invention further relates to a preferred method of testing with a test device wherein a first reagent composition in the device which is reactive with a second reagent composition applied to the device in a liquid carrier produces an identifiable color which comprises providing a test device with a solid body of thermoplastic resin which is soluble in the liquid carrier for the second reagent composition at ambient temperatures admixed with the first reagent composition in an amount sufficient for at least a qualitative colorimetric detection of the second reagent composition which is applied to an exposed surface of the resin in the liquid carrier and dissolves the resin at the surface without permeating the body of the resin; and applying the second reagent composition to an exposed surface of the resin so that some liquid remains on the surface thereby providing the reacted first and second reagents on the exposed surface in the liquid carrier and dissolved resin.

The primary purposes and objectives of the invention are accomplished by:

1. providing encapsulated inorganic and organic colorimetric indicator reagent compositions in a three-dimensional solid, porous or non-porous composition by using a thermoplastic resin. The invention provides the means whereby the reaction between the encapsulated first reagent composition, which can be regarded as one of a pair or more of chromogenic materials, and the second reagent composition in a liquid carrier which solventizes the resin is predictable, precise and discernible because it is isolated at an exposed surface of the resin. Thus, by incorporating the first reagent composition into the thermoplastic resin, the resulting indicator device functions at the surface of application dissolved by the liquid carrier as the substrate and first reagent composition source for the qualitative and/or quantitative determination of a second reagent composition.

2. providing colorimetric indicator compositions which can be processed using conventional methods and equipment for the bonding of thermoplastic particles. For example: injection, compression, blow, extrusion, hot melt moulding as well as film casting can be used. The advantage of processing by the thermoplastic bonding of particles is one of economics, due largely to production efficiency and minimal capital investment in the development of processing equipment. This is in contrast to the current methods of manufacturing paper colorimetric indicator devices which utilize a multi-phase procedure for impregnating paper with specific first reagent compositions, cutting and then adhering the paper to inert plastic strip or other inert support strip means.

3. providing a first reagent composition delivery system via an indicator device which can be scraped, rinsed or wiped off and rendered reusable. This is in contrast to currently available devices which use the conventional porous testing device (whether it be tablet or impregnated paper) and must be discarded after one use. Thus, economic considerations apply not only to the manufacturing process but also to the use of the test device.

COLORIMETRIC REAGENTS

The present invention uses known technology in the colorimetric indicator art where first reagent and second reagent compositions react to form an identifiable color. Thus, for instance, there are indicator color changes involving acid or base reactions; oxidation or reduction reactions; precipitation reactions and complex formation reactions. The production of such indicator color changes is very well known to those skilled in the art and is described for instance in Kirk-Othmer, Encyclopedia of Chemical Technology, (Second Edition) Volume 11 (1966) John Wiley & Sons, Inc. at pages 548 to 561 and in the patent art.

As used in regard to the present invention the term "colorimetric" means the detection of a change in color as a result of the reaction of the first and seond reagent compositions. The change can be at least qualitatively detected and in some instances a quantitative evaluation can be made as a function of the intensity of the color change.

RESINS

The thermoplastic resins which are useful in preparing the colorimetric indicators of the present invention have the common physical characteristic of being soluble in the liquid carriers for the second reagent composition, usually water, lower alkanols or other polar organic solvents, at ambient temperatures. The water soluble resins which are preferred are generally synthetic since natural resins are usually water insoluble. The resins can be long chain polymers or they can be derived from purified or chemically modified naturally occurring materials, such as chemically modified cellulose. The resins must not interfere with the reaction of colorimetric indicator reagents. The resins can be plasticized to make them more moldable. In order to be readily moldable, the resins are thermoplastic, which means that particles can be molded and bonded together with heat to form a solid, non-porous body of resin. Thermoplastic resins are easily solventized by comparison to thermoset resins which are difficult to solventize once they are cured. The selection of thermoplastic resins for use in the present invention is easily within the skill of the art.

The preferred water soluble thermoplastic resin is hydroxypropyl cellulose (HPC). It is described in U.S. Pat. Nos. 2,523,377 and 2,572,039 and in the 1971 product literature of Hercules Incorporated and it is sold under the trademark Klucel. HPC is also described in an article in Food Technology, Vol. 24, No. 1, pages 51 to 54 (1970). HPC is the ether reaction product of propylene oxide with the reactive hydroxyl groups in cellulose. Based upon the available hydroxyl groups there are theoretically up to three propylene oxide units per anhydroglucose monomer unit of the cellulose (M.S. 3.0), however, the propylene oxide polymerizes with itself to give a higher degree of substitution. The preferred resins have a molecular weight between about 60,000 and 1,000,000 and an M.S. between 2.0 and 10 with 3 to 4.5 being preferred. It can be injection molded and is heat sealable in films and coatings and softens at 130°C. The resin is non-ionic and is soluble in water and in many polar organic solvents. It is soluble in water below 40°C and insoluble in water above 40° to 45°C. It is soluble in acetylated monoglycerides, polyethylene glycols, polypropylene glycol, pure oil and tail oil and fatty acids. It is partially or completely soluble in the solvents shown in Table I.

TABLE I

| | |
|---|---|
| Water | Dioxane |
| Methyl alcohol | Dimethyl sulfoxide |
| Ethyl alcohol | Dimethyl formamide |
| Isopropyl alcohol (95%) | Ethylene chlorohydrin |
| Propylene glycol | Tetrahydrofuran |
| Methyl Cellosolve | Cyclohexanone |
| Cellosolve | t-Butanol:water (9:1) |
| Chloroform | Acetone:water (9:1) |
| Formic acid (88%) | Glycerin:water (3:7) |
| Acetic acid (glacial) | Benzene:methanol (1:1) |
| Pyridine | Toluene:ethanol (3:2) |
| Morpholine | Methylene chloride: methanol (9:1) |
| Tertiary butanol | Methylene chloride |
| Cyclohexanol | Butyl acetate |
| Acetone | Butyl Cellosolve |
| Methyl ethyl ketone | Lactic acid |
| Methyl acetate | Naphtha:ethanol (1:1) |
| Isopropyl alcohol (99%) | Xylene:isopropyl alcohol (1:3) |

Small amounts of plasticizers can be used with HPC to provide flexibility and softness. These are for instance: propylene glycol, glycerin, polyethylene glycols and trimethyl propane. Small amounts of molding lubricants can also be used, such as glycerol monostearate, silicones, lecithin and various stearates. Known antioxidants and preservatives can also be used. Fillers and compatible polymers can also be used as extenders, so long as these ingredients do not interfere with the essential purpose of colorimetric indication. Loadings of 40 to 95 by weight percent fillers in HPC can be used. HPC can be injection and compression molded, blow molded, injection foam molded, vacuum formed and extruded.

Another class of preferred water soluble thermoplastic resins is the polyethylene glycol resins. These products are sold under the trademark Carbowax. The resins are described in product literature of Union Carbide Corporation which is dated 1972. They are polymers of the monomer ethylene oxide and have the formula:

$$HOCH_2(CH_2OCH_2)_xCH_2OH$$

The available hydroxyl groups in the polymer can be used to prepare esters or ethers (e.g. methoxypolyethylene glycols). The resin is soluble in water and in many organic solvents. The resin can be stabilized using known antioxidants. It can be thermoplastically molded in the same manner as HPC.

Another preferred class of resins is the polyethylene oxide resins. These resins are sold under the trademark Polyox. They are described in product literature of Union Carbide Corporation which is dated 1968. These resins are water soluble as well as being soluble in many organic solvents. They can be molded like HPC.

U.S. Pat. Nos. 3,070,451 and 3,124,474 describe plasticized hydroxyl alkyl alkyl celluloses which are water soluble and which can be molded because of the use of certain plasticizers. These plasticized resins can also be used.

The ratio of resin to first reagent composition can be between about 10,000 to 1 and 1.0 to 1.0. Usually the least amount of indicator which will reproducibly produce the desired colorimetric reaction is sufficient and is preferred for economic reasons.

METHOD

The first reagent composition of the colorimetric reagents is dispersed in the resin. This can be accomplished by encapsulating the first reagent composition using conventional techniques and materials, mixing the encapsulated reagent composition with the resin and then molding or casting the indicator composition. For reasons of economy and because of superior results in manufacturing, it is greatly preferred that particles of the resin be coated with the first reagent composition. The particles can then be bonded together.

In the preferred method as illustrated in FIG. 1, the coating of the particles of the resin can be accomplished by either providing the first reagent composition as a powder which is dusted on the particles of the polymer or by providing a liquid solution or dispersion of the first reagent composition which is applied on the particles. It has been found that this is the most economical way to provide the first reagent composition in the resin. In addition, test results on the product from the preferred method indicate that the definition of color is sharp, probably because the bodies of resin between the islands of the first reagent composition aid in providing a background for the reacted colorimetric reagent compositions.

The particle size of the resin is not critical except to the extent that sufficient first reagent composition must be provided at an exposed surface of composition to be used for testing. In general a particle size between about 0.01 and 10 millimeters is preferred. The resins are normally supplied as particles in this size range from the manufacturers.

The thermoplastic molding of the resins is within the knowledge of the art. It is preferred for reasons of economics to injection, compression, film cast, blow, or extrusion mold the coated particles, since these and other methods are very rapid and the equipment is readily available. The molded resin which is waste from the formation of the colorimetric indicators can be ground into particles and recycled in a manner which is conventional practice for molding.

COLORING AGENTS

The preferred colorimetric compositions of the present invention incorporate a coloring agent which provides a color contrast by forming a dispersed particle background in the liquid carrier for the second reagent composition. This component is particularly preferred because in many instances the combination of only the first reagent composition and certain resins produces a product which is colored before use and this color tends to mask the results of the colorimetric reaction with the second reagent composition in use.

The coloring agents are generally inert at least to the first reagent composition and to the resin and thus act much like fillers in the compositions of the present invention. The coloring agents are also generally not reactive with the second reagent composition, although the coloring agent can be complexed, oxidized or reduced by the second reagent composition to provide a better color contrast.

It is only necessary that the coloring agent be present at the exposed surface of the composition to be used for a colorimetric test. Thus it can be dusted only on the surface which is an economical way of providing the coloring agent. If the composition is to be used by dipping into the second reagent composition liquid carrier, then the particles of the coloring agent can be bonded onto or impregnated into the surface with a resin which is solventized by the liquid carrier for the second reagent to prevent them from being washed from the surface. Alternatively, the coloring agent can be mixed with the resin or preferably coated on particles of the resin with the first reagent composition prior to molding. The latter method is preferred for reasons of economics.

The color of the coloring agent is not critical so long as it provides an adequate background contrast for the reacted colorimetric indicator reagent compositions. In most instances white is preferred, since it usually provides the necessary contrast.

The particle size of the coloring agent is not critical, so long as it provides the necessary background contrast within the surface area where the liquid carrier and second reagent composition is to be applied. Particle sizes between about 0.0001 and 0.5 millimeter are preferred.

The weight ratio of particles of coloring agent to resin between about 1:250 and 1:1. The least amount which reproducibly and reliably produces the desired contrast is preferred.

ABSORBANT FILLER MATERIALS

It is also preferred to incorporate a small amount of particles of an absorbant filler material in contact with the first reagent composition coated resin particles prior to bonding the particles. The absorbant filler material functions to improve and increase the rate of the penetration of the second reagent composition into the surface of the indicator composition where the first reagent composition is located to improve color development. These filler materials are not soluble in the liquid carrier containing the second reagent composition. They are generally finely divided fibers and probably function by capillary action to allow the liquid carrier to penetrate slightly into the surface of the indicator composition. They usually have a particle size between about 0.0001 and 0.05 millimeter and are used in amounts between about 0.01 and 0.5 parts by weight of thermoplastic resin.

DESCRIPTION OF PREFERRED EMBODIMENTS

The following examples are only intended to be illustrative of the present invention. In Examples I to X, the method of processing was the same. An aqueous slurry of the ingredients, which is the first reagent composition designated as "Composition A", was prepared. Small amounts of water were used to allow for uniformly coating particles of the water soluble resin with the first reagent without dissolving it. Composition A was then tumble mixed with "Composition B" which consisted of HPC (Klucel Type J), having a particle size of 2 to 5 millimeters so as to coat the resin particles. Composition B included any necessary fillers, plasticizers, preservatives and the like. If the absorbant fillers were to be used, these were added as "Composition C" and tumble mixed with the Composition A and B coated particles. If the coloring agent was to be used, this was designated as "Composition D" and was tumble mixed with the mixture of Compositions A and B before mixing with Composition C. After mixing, the resulting composition was plastic molded under pressure (40°C to 121°C at 100 to 2000 psig). The products were then formed into sheets or strips about 2 millimeters thick and 25 millimeters wide which were used for testing. The sheets were also used for fabricating the test strips described hereinafter.

Representative colorimetric indicator compositions which are sensitive to pH and the range of the amounts of the ingredients used are listed in Table II.

TABLE II

| Composition | Ingredient | | Amounts (Weight % of Total Weight) |
|---|---|---|---|
| A | pH Responsive First Reagent Composition | | .01%–10% |
| | There are many and include the following: | | |
| | cresol red | methyl violet | |
| | metacresol purple | theynol blue | |
| | methyl violet | tetrabromphenol blue | |
| | bromophenol blue | bromocresol green | |
| | methyl red | methyl purple | |
| | bromocresol purple | chlorophenol red | |
| | bromothynol blue | phenol red | |
| | phenolphthalein | o-cresolphthalein | |
| | alizarin yellow GG | sulfo orange | |
| | methyl yellow | neutral red | |
| | rosalic acid | alizarin blue S | |
| | tetrabromphenolphthalein | ethyl ester | |
| A₁ | *Liquid Dispersing Agent | | |
| | Water | | 1–10% |
| B | Water Soluble Thermoplastic Resins | | 20%–99.99% |
| | hydroxypropyl cellulose (Klucel) | | |
| | polyethylene oxide (Polyox) | | |
| | polyethylene glycol (Carbowax) | | |
| B₁ | Optional Fillers in HPC Resin | | |

TABLE II-continued

| Composition | Ingredient | Amounts (Weight % of Total Weight) |
|---|---|---|
| | Plastic: | 1–90% |
| | polyethylene | |
| | polystyrene | |
| | polypropylene | |
| | butadiene-styrene block copolymer | |
| | Powders: | 1–50% |
| | bentonite | |
| | clay | |
| | aluminum silicate | |
| | pumice | |
| | silicates and silicon dioxide | |
| $B_2$ | Optional HPC Plasticizers | 1–5% |
| | propylene glycol | |
| | triacetin | |
| | dioxane | |
| | 2-ethoxy-ethanol (cellusolve) | |
| | 2-methoxy ethanol | |
| C | Optional Absorbant Filler Materials | 1–50% |
| | perlite          asbestos | |
| | purified wood cellulose | |
| | silicon dioxide | |
| | filter aids | |
| | molecular sieves | |
| $C_1$ | *Anti-Caking Material (added to resin wetted | |
| | with dispersing agent) | |
| | silicon dioxide or molecular sieve zeolites | |
| | (the percent depends upon | |
| | amount of water added to | |
| | the resin particles in order to | |
| | make them free flowing for plastic | |
| | molding) | |
| D | Optional Coloring Agents (Preferred White) | 1–50% |
| | titanium dioxide          calcium sulfate | |
| | calcium carbonate      calcium oxide | |
| | zinc oxide                    zinc sulfate | |
| | stannic oxide              barium sulfate | |
| | zirconium oxide | |
| | zirconium silicate | |
| | mica | |
| | silica | |
| | diatomaceous earth | |
| | talc | |

*The utilization of these groups is preferred in the method of manufacturing.

For the colorimetric indicators containing a pH responsive first reagent composition, an item from each of the functional groups listed in Table II other than A and B is unnecessary in order to make the indicator work. For instance, indicators were prepared which contained only the following ingredients:
1. (Composition A) - pH responsive chromogenic indicator (one of the following)
   a. tetrabromophenol blue;
   b. phenolphthalein;
   c. bromocresol purple;
   d. bromocresol green; or
   e. bromthmol blue
2. (Composition B) Water soluble thermoplastic resin - hydroxypropyl cellulose; and optionally with
3. (Composition D) Coloring agent (white) - titanium dioxide.

Materials from groups other than the Composition B resins, the Composition A first reagent compositions and the preferred Composition C coloring agents may be desirable to produce specific end-product properties and to facilitate the ease of manufacture and minimize raw material costs, such as the use of relatively inexpensive fillers. The use of these materials applies also to the indicators which are shown in the Examples.

In the following Examples, testing of the indicators was by applying water as the carrier liquid containing the acid or the base as the second reagent composition on an exposed surface to produce color contrast. The titanium dioxide coloring agent particles (particle size of less than 0.05 millimeter 325 International Mesh Size) formed a white background at the surface of the resin where the water was applied. The HPC had a particle size of 2 to 5 millimeters.

Example I

Alkaline Solutions Test
(Colorless to pink)

| Composition | Ingredient | Wt. (grams) | Percent by Weight of Total Weight |
|---|---|---|---|
| A | phenophthalein | 2.5 | 0.5% |
| B | hydroxypropyl cellulose (HPC) | 40 | 8.0% |
| $B_1$ | diluent butadiene-styrene block copolymer | 377.5 | 75.5% |
| $B_2$ | plasticizer - triacetin | 25 | 5.0% |
| C | permeability aid molecular sieve zeolite | 50 | 10.0% |
| D | titanium dioxide | 5 | 1.0% |

Example I-continued

Alkaline Solutions Test
(Colorless to pink)

| Composition | Ingredient | Wt. (grams) | Percent by Weight of Total Weight |
|---|---|---|---|
| | | 500 gms | 100.0% |

Example II

Urine pH Test
(Wide range pH 4.5 – 9.0 (orange to blue))

| Composition | Ingredient | Wt. (grams) | Percent by Weight of Total Weight |
|---|---|---|---|
| A | bromthymol blue | .75 | 0.15% |
| A | methyl red | .75 | 0.15% |
| B | HPC | 233.50 | 46.70% |
| C | silicon dioxide | 250 | 50.0% |
| D | titanium dioxide | 15 | 3.0% |
| | | 500 gms | 100.0% |

Example III

Protein Test
(Background information for this test is found in U.S. Pat. No. 3,438,737)

| Composition | Ingredient | Wt. (grams) | Percent by Weight of Total Weight |
|---|---|---|---|
| A | sodium citrate | 5.0 | 0.95 |
| A | citric acid | 9.0 | 1.7 |
| A | tetrabromphenol blue | 0.15 | 0.03 |
| A | triacetin | 5 | 0.95 |
| $A_1$ | water | 5 | 0.95 |
| B | HPC | 400 | 76.35 |
| C | perlite, silicate | 100 | 19.07 |
| | | 524.15 | 100.0% |

The ingredients of Composition A were blended with stirring but after 10 minutes the slurry "set up" and became granular due probably to salt-water ratio which produced a "salting out". This would not have occurred if slurry was added immediately to Composition B. Composition A was then added to Composition B and tumbled so as to coat the HPC particles with Composition A. Composition C was added to Compositions A and B and tumbled. The resulting mixture was free flowing and Composition A appeared to be homogeneously dispersed. The injection molded part (220°F, 2000 psi) was emerald green and translucent.

An extruded filament was yellow-green initially but turned light blue after 3 to 4 hours. This suggested that there was not enough citric acid in formation; however, it did produce acceptable test results.

Standard stock second reagent composition solutions of protein containing 50 and 100 mg protein per 100 milliliters of water as the liquid carriers were used. A drop of each solution was placed upon a sample of the composition. A procedure whereby the sample was dipped into the solution was also used.

No color change was grossly apparent on either of the samples whether the "drop" or "dip" procedure was used. That is, the expected color change from yellow to blue was not discernible. However, when the wetted surface was scraped off, the color of the scraping was blue. The question was how the chromogenic response be detected without the scraping step when first reagent Composition A was acted upon by the protein (second reagent composition) test solution.

EXAMPLE IV

This product was similar to Example III but with more water (10 gms) as the dispersing agent $A_1$, and more absorbant filler C (200 gms). Also added polypropylene $B_1$ (100 gms) was used. The result was the same as Example III.

EXAMPLE V

This product was similar to Example III but with silica C (100 gms) and silicate C (perlite, 100 gms) and to increase the permeability of the resin at the surface of the product. The result was the same as Example III.

EXAMPLE VI

The surface of the product of Example III was dusted with titanium dioxide D prior to testing and it turned white. When the protein solution (second reagent composition) was added, the surface turned blue. The titanium dioxide provided an excellent color contrast in the resin dissolved at the surface by the water.

Example VII (Protein test procedure of U.S. Pat. No. 3,438,737)

| Composition | Ingredient | Wt. (grams) | Percent by Weight of Total Weight |
|---|---|---|---|
| A | sodium citrate | 5 | 0.4 |
| A | citric acid | 62 | 4.6 |
| A | tetrabromphenol blue | 0.5 | 0.04 |
| A | ethanol | 5 | 0.4 |
| A | triacetin | 25 | 2.0 |
| $A_1$ | water | 30 | 2.3 |
| B | HPC | 600 | 45 |
| C | silica | 300 | 22.76 |
| C | perlite | 50 | 3.7 |
| D | titanium dioxide | 250 | 18.8 |
| | | 1327.5 | 100 |

Compositions A and B were blended and Composition D was added. The mixture was a creamy-yellow color. Composition C was added and the mixture was tumbled. The mixture was free-flowing. After the mixture was extruded, it was immediately compressed between two metal plates to a thickness of 2 millimeters.

Test Results: The composition worked well; however, the colors were pastel because of more titanium dioxide than was necessary.

Example VIII (Example VII with less titanium dioxide)

| Composition | Ingredient | Wt. (grams) | Percent by Weight of Total Weight |
|---|---|---|---|
| A | sodium citrate | 3.0 | 0.55 |
| A | citric acid | 33.0 | 6.0 |
| A | tetrabromphenol blue | 0.3 | 0.05 |
| A | triacetin | 15 | 2.6 |
| $A_1$ | water | 15 | 2.6 |
| B | HPC | 300 | 52.0 |

Example VIII-continued (Example VII with less titanium dioxide)

| Composition | Ingredient | Wt. (grams) | Percent by Weight of Total Weight |
|---|---|---|---|
| C | silica | 175 | 30.0 |
| C | perlite | 25 | 4.5 |
| D | titanium dioxide | 10.0 | 1.7 |
| | | 576.3 | 100% |

The product was blended, extruded, and compressed as in Example VII. The test results were the same as described in U.S. Pat. No. 3,438,737. Using standard urine-protein solutions the colorimetric response to protein was more vividly defined than the product described in U.S. Pat. No. 3,438,737, but the reaction of the prior art product was more rapid. A short period of time of 5 to 10 seconds was necessary for the water to solventize the HPC resin which does not create problems in use. The water soluble resins are preferred since they can be solventized in the shortest period of time.

EXAMPLE IX: KETONE TEST DEVICE

The manufacturing procedure was the same as for the protein test device of Examples III to VIII.

The following formulation was prepared and extruded:

| Composition | Ingredients | Wt. (grams) | Percent by Weight of Total Weight |
|---|---|---|---|
| A + A$_1$ | sodium nitroprusside (saturated aqueous solution) | 20 | 5.6 |
| A | sodium monophosphate | 10 | 2.7 |
| A | glycine | 23 | 6.0 |
| A$_1$ | water | 5 | 1.3 |
| B | HPC | 200 | 54.5 |
| B | aluminium oxide | 100 | 27.2 |
| D | titanium dioxide | 10 | 2.7 |
| | | 368 | 100% |

The extruded filament was tested via the "drop" or "dip" methods for ketones using standard solutions containing 50, 100 and 1000 mg ketone per 100 ml of solution. The colorimetric response was negative, pink, purple, deep violet with the increasing concentrations of ketone.

EXAMPLE X

Aceto-acetic Acid Test Device

This device has limited use since the ketone stick of Example IX which is better.

| Composition | Ingredient | Wt. (grams) | Percent by Weight of Total Weight |
|---|---|---|---|
| A + A$_1$ | 45% iron chloride solution (aqueous) | 20 | 4.7 |
| B | HPC | 300 | 70 |
| C | silicon dioxide | 100 | 23.2 |
| D | titanium dioxide | 10 | 2.1 |
| | | 430 | 100% |

Prepared as in Example I. The device was tested with standard solutions containing aceto-acetic acid which when deposited on the composition produced purple-violet color.

Figure 2:
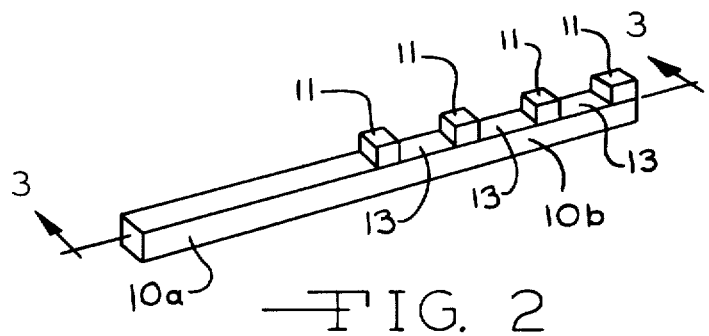
FIG. 2 is a perspective view of a preferred test strip particularly illustrating multiple tabs which may contain the same or a different first reagent composition for colorimetric testing.
Figure 3:
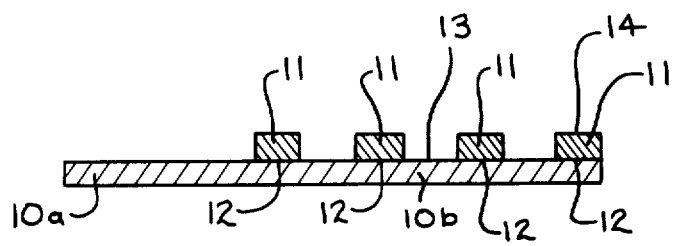
FIG. 3 is a cross-sectional front view of FIG. 2 along line 3—3 of the preferred test strip, particularly illustrating the points of thermoplastic fusion of the tabs with the body portion of the strip.

FIGS. 2 and 3, a preferred test strip or stick 10 is shown including a handle 10a and a mounting portion 10b. The colorimetric indicator tabs 11 are bonded to the mounting portion 10b at the interface 12. Preferably the material at least at the surface of the mounting portion 10b of the stick is composed of a thermoplastic resin so that heat fusion bonding can be used at interface 12 to joint the tabs 11 to the mounting portion 10b of the stick. Spaces 13 are provided between each tab 11 so that the tests at each tab 11 can be separate. The surfaces 14 of the tabs 11 are where the liquid carrier containing the second reagent composition is to be applied.

Figure 4:
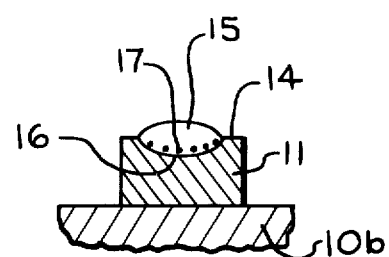
FIG. 4 is a cross-sectional front view of an individual tab, particularly illustrating a liquid carrier for the second reagent composition on the thermoplastic resin, with dispersed particles of a coloring agent which contrasts with the color of the reacted reagents in a depression dissolved by the liquid carrier.
Figure 5:
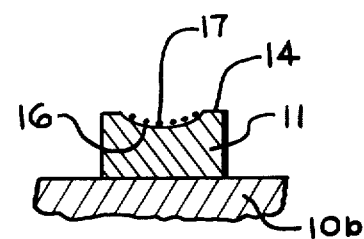
FIG. 5 is a cross-sectional front view of an individual tab, particularly illustrating the depression shown in FIG. 4 with the liquid carrier removed and with the coloring agent and reacted reagents at the bottom of the depression.

FIG. 4 shows an individual tab 11 with a drop 15 of the liquid carrier for the second reagent composition. The drop 15 of the liquid carrier dissolves a portion of the tab 11 leaving an indentation 16. The particles 17 of the preferred coloring agent are exposed in this indentation 16. In FIG. 5, the drop 15 of the carrier liquid is removed from the tab 11, such as by drying, preferably leaving the coloring agent particles 17 which are coated with the reacted colorimetric indicator reagent compositions. The tab 11 in FIG. 5 can be preserved for future reference, after removal of the liquid carrier.

Figure 6:
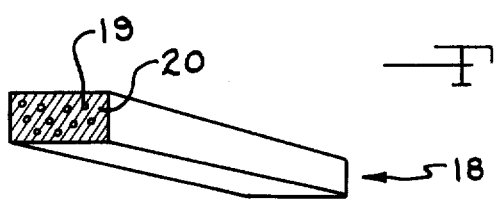
FIG. 6 is a cross-sectional enlarged view of a stick of thermoplastic resin, schematically illustrating islands of the first reagent composition dispersed in the thermoplastic resin.

FIG. 6 is an enlarged cross-section illustrating internal composition of an unsupported stick 18. The first reagent composition is encapsulated as islands 19 in the thermoplastic resin 20. A portion of the stick 18 can function as a handle. The first reagent composition 19 as well as optional fillers and coloring agents are thus heterogeneously encapsulated in the resin 20.

It will be appreciated that the second reagent composition can be supplied in a gas which contains vaporized liquid carrier which solventizes the surface of the colorimetric indicator tab at elevated or reduced ambient temperatures. Such devices could be used for detecting the presence of humidity, air pollutants and the like.

Preferably the indicators will be used at air ambient temperatures; however, they can be used in systems operating at higher and lower tamperatures so long as there is a colorimetric change. Numerous other obvious variations will occur to those skilled in the art.

We claim:

1. The article of manufacture useful as a colorimetric indicator which comprises:
   a. a first reagent composition which is reactive with a second reagent composition contained in a liquid carrier to produce an identifiable color; and
   b. a solid body of a water soluble thermoplastic resin which is also soluble in the liquid carrier for the second reagent composition at ambient temperatures admixed with the first reagent composition in an amount sufficient for at least a qualitative colorimetric detection of the second reagent composition in the liquid carrier which is applied to an exposed surface of the resin and dissolves the resin at the surface without permeating the body of the resin.

2. The article of claim 1 wherein the resin is a water soluble hydroxypropyl cellulose, polyethylene oxide or polyethylene glycol or mixtures thereof to be used with water as the liquid carrier for the second reagent composition.

3. The article of claim 1 wherein the first reagent composition is dispersed throughout the resin between bodies of thermoplastically bonded particles of resin.

4. The article of claim 1 which in addition contains at least at an exposed surface of the resin an amount of particles of a coloring agent which when the first and second reagents react provides a color contrast by forming a dispersed particle background in the liquid carrier for the second reagent composition.

5. The article of claim 4 wherein the particles of the coloring agent are white.

6. The article of claim 5 wherein the particles of the coloring agent are composed of titanium dioxide.

7. The article of claim 4 wherein the first reagent composition and the coloring agent particles are dispersed in islands throughout the resin between bodies of pure resin.

8. The article of claim 4 wherein the weight ratio of particles of coloring agent to resin is between about 1:100 and 1:1.

9. The article of claim 1 wherein the weight ratio of resin to first reagent composition is between about 10,000 and 1 to 1.

10. The article of claim 1 wherein an absorbant filler material which is insoluble in the liquid carrier is associated with the first reagent composition to improve the color detection.

11. The article of claim 1 wherein an absorbant filler material which is insoluble in the liquid carrier is associated with the first reagent composition in a ratio of filler material to resin of between about 0.01 and 0.5 parts by weight to improve the color detection.

12. The article of claim 11 wherein the absorbant filler material is powdered silica.

13. The article of claim 5 which contains a water soluble hydroxypropyl cellulose as the thermoplastic resin and titanium dioxide as the coloring agent.

14. The method of manufacturing an article of manufacture useful as a colorimetric indicator which comprises:
   a. a first reagent composition which is reactive with a second reagent composition applied in a liquid carrier to produce an identifiable color;
   b. coating particles of a thermoplastic resin which is soluble in the liquid carrier for the second reagent composition at ambient temperatures with the first reagent composition; and
   c. thermoplastically bonding the particles together into a solid body so that the first reagent composition is dispersed in islands throughout the resin, the amount of first reagent composition being sufficient for at least a qualitative colorimetric detection of a liquid carrier containing the second reagent which is applied to an exposed surface in the liquid carrier and which dissolves the resin at the surface without permeating the body of the resin.

15. The method of claim 14 wherein particles of a coloring agent are provided on at least an exposed surface of the resin in an amount and particle size such that when the first and second reagent compositions react the agent provides a color contrast by forming a dispersed particle background in the liquid carrier from the second reagent.

16. The method of claim 15 wherein the coloring agent particles are coated on the resin particles after application of the first reagent composition to the resin particles and before thermoplastic bonding.

17. The method of claim 14 wherein the bonded resin and first reagent composition body is thermoplastically bonded to a thermoplastic material strip having a handle.

18. The method of claim 14 wherein the first reagent composition is coated on the resin particles while being dispersed in a liquid carrier which is a solvent for the resin.

19. The method of claim 14 wherein the particles are thermoplastically bonded together by plastic molding procedures including injection and extrusion.

20. The method of testing with a test device wherein a first reagent composition in the device which is reactive with a second reagent composition applied in a liquid carrier to the device produces an identifiable color which comprises:
   a. providing a test device with a solid body of thermoplastic resin which is soluble in the liquid carrier for the second reagent composition at ambient temperature admixed with the first reagent composition in an amount sufficient for at least a qualitative colorimetric detection of the second reagent composition in the liquid carrier which is applied to an exposed surface of the resin and dissolves the resin at the surface without permeating the body of the resin; and
   b. applying the second reagent composition to an exposed surface of the resin so that some liquid carrier remains on the surface thereby providing the reacted first and second reagents compositions on the exposed surface in the liquid carrier and dissolved resin.

21. The method of claim 20 wherein in addition the liquid carrier is evaporated to fix the reacted reagents on the surface.

22. The method of claim 20 wherein the liquid carrier is water and the resin is water soluble.

23. The method of claim 20 wherein the device is dipped into the liquid carrier with the second reagent composition.

24. The method of claim 20 wherein a drop of the liquid carrier with the second reagent composition is applied to an exposed surface of the device.

25. The method of claim 20 wherein the liquid carrier is applied as a vapor in a gas containing the second reagent which is contacted with the surface of the device to condense and dissolve the resin.

26. The method of claim 25 wherein the gas is air.

27. The test device wherein a first reagent composition in the device reacts with a second reagent composition applied in a liquid carrier to the device to produce an identifiable color which comprises:
   a. a support strip including a handle and a body portions;
   b. at least one part provided on the body portion and being comprised of a solid body of a water soluble thermoplastic resin which is also soluble in the liquid carrier for the second reagent composition at ambient temperatures in admixture with the first reagent composition in an amount sufficient for at least a qualitative colorimetric detection of the second reagent composition which is applied to an exposed surface of the resin in the liquid carrier which dissolves the resin at the surface without permeating the body of the resin.

28. The test device of claim 27 wherein at least the exposed surface of the tab to which the second reagent composition in the liquid carrier is to be applied contains an amount of particles of a coloring agent which when the first and second reagent compositions react provides a color contrast by forming a dispersed particle background in the liquid carrier from the second reagent composition which dissolves the resin at the surface of application.

29. The test device of claim 27 wherein the strip is composed of a thermoplastic resin which is thermoplastically bonded to the tab.

* * * * *